(12) United States Patent
Horita

(10) Patent No.: US 7,911,613 B2
(45) Date of Patent: Mar. 22, 2011

(54) METHOD AND SYSTEM FOR PREDICTING PRINT COLORS

(75) Inventor: Shuhei Horita, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 252 days.

(21) Appl. No.: 12/144,343

(22) Filed: Jun. 23, 2008

(65) Prior Publication Data

US 2009/0021738 A1  Jan. 22, 2009

(30) Foreign Application Priority Data

Jul. 17, 2007  (JP) ................................. 2007-185821

(51) Int. Cl.
*G01J 3/40* (2006.01)
(52) U.S. Cl. ......... 356/404; 356/402; 356/408; 356/425
(58) Field of Classification Search ........................ None
See application file for complete search history.

(56) References Cited

U.S. PATENT DOCUMENTS 7,166,422 B2 * 1/2007 Nakahira et al. .............. 430/505
7,543,922 B2 * 6/2009 Kachi ............................ 347/84

FOREIGN PATENT DOCUMENTS

JP  2004-230793 A  8/2004
JP  2004-251848 A  9/2004

* cited by examiner

*Primary Examiner* — Sang Nguyen
(74) *Attorney, Agent, or Firm* — Sughrue Mion, PLLC

(57) ABSTRACT

A colorimeter of a profile generator calorimetrically measures a color chart after elapse of a sufficient period of time from printing of the color chart, thereby producing post-dry-down colorimetric values. The colorimeter also calorimetrically measures certain patches selected from the color chart immediately after printing thereof, thereby producing pre-dry-down calorimetric values. Colorimetric value differences between the post-dry-down colorimetric values and the pre-dry-down colorimetric values are calculated. Using the calorimetric value differences and the post-dry-down calorimetric values, device-dependent data are converted into colorimetric values, which represent pre-dry-down device-independent data. The colors of a print prior to dry-down are predicted based on such converted colorimetric values.

7 Claims, 14 Drawing Sheets

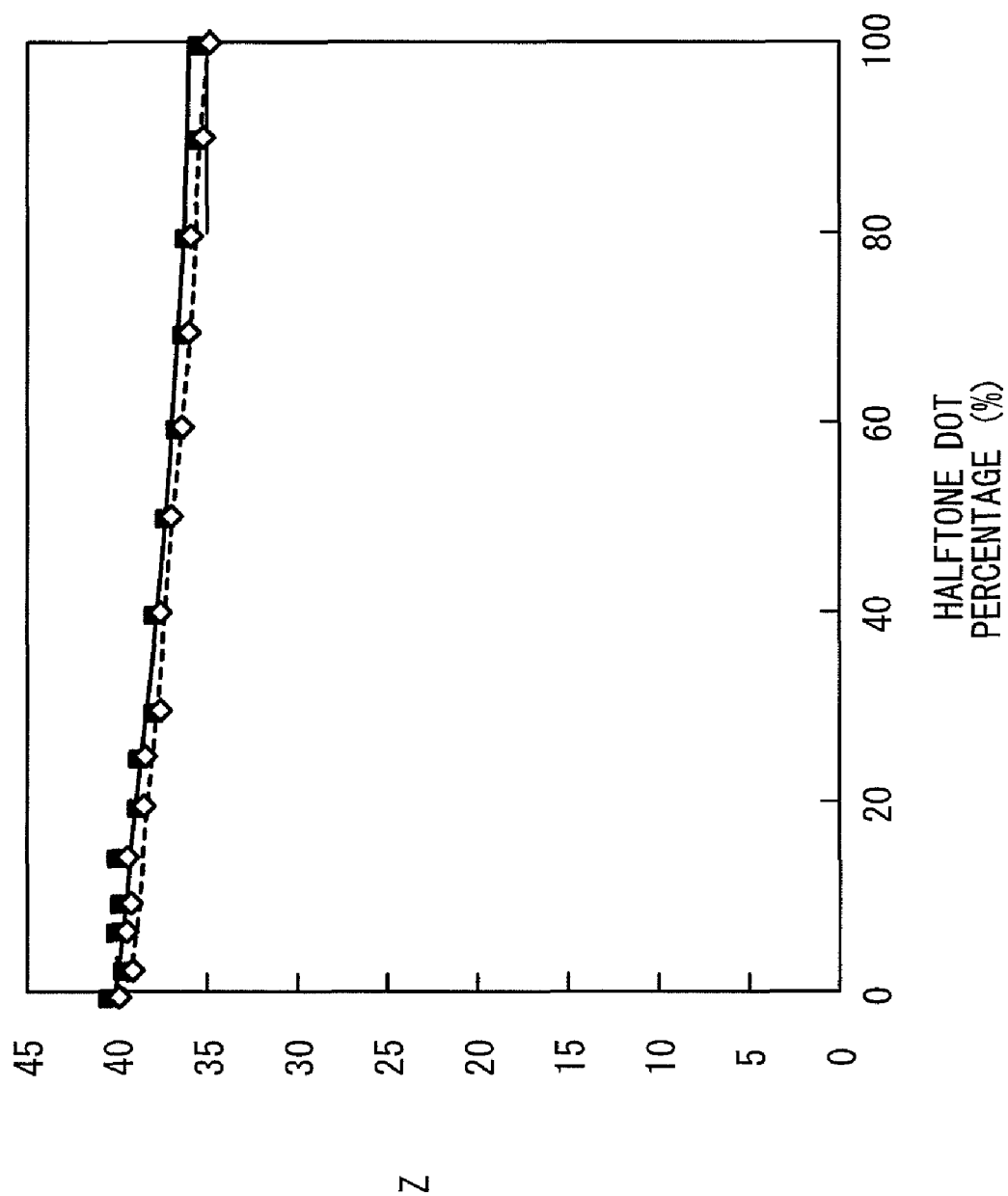

METHOD AND SYSTEM FOR PREDICTING PRINT COLORS

BACKGROUND OF THE INVENTION

1. Field of the Invention

The present invention relates to a method and system for predicting the print colors of a print produced by a printing press.

2. Description of the Related Art

Prints are produced by generating original film plates in various colors including cyan (C), magenta (M), yellow (Y), and black (K), for example, producing PS plates (presensitized plates) from the original film plates by exposure and development, mounting the PS plates on a printing press such as a rotary press or the like, and adjusting printing conditions, including printing pressure, dampening water, temperature, etc.

Therefore, complex steps are involved in producing prints. In order to produce a print having desired colors, it has been customary, prior to the production of the print, to generate a proof sheet using a simple output device such as a color printer or the like, confirm the generated proof sheet, and adjust printing conditions.

The colors of a print immediately after it has been printed and the colors of the same print upon elapse of a certain period of time after printing are different from each other, because the inks penetrate into the print sheet and are dried over time. This phenomenon is generally referred to as dry-down.

FIG. 8 of the accompanying drawings shows a graph having a horizontal axis representing a time in minutes that has elapsed after a print is produced, and a vertical axis representing a color difference dE from a color upon elapse of a sufficient period of time from the production of the print. It can be seen from FIG. 8 that the color difference dE varies greatly immediately after each of the inks in the colors C, M, Y, K has been printed. The variation of the color difference dE becomes smaller as the time in minutes elapses. The color difference dE also differs from ink to ink.

As shown in FIGS. 9, 10 and 11 of the accompanying drawings, if the print colors are expressed by colorimetric values L*, a*, b*, then on each of an a*b* plane, an L*a* plane, and an L*b* plane, the color gamut of the print, indicated by the dotted-line curve, prior to dry-down immediately after the print is produced is reduced to the color gamut of the print, as indicated by the solid-line curve, subsequent to dry-down. Particularly, the reduction of the color gamut stands out in shadows.

As shown in FIGS. 12, 13 and 14 of the accompanying drawings, if the print colors are expressed by calorimetric values X, Y, Z in graphs having horizontal axes representing a halftone dot percentage (%) and vertical axes representing the colorimetric values X, Y, Z, then the colorimetric values X, Y, Z change, so as to become increased from the values indicated by the dotted-line curve prior to dry-down to the values indicated by the solid-line curve after dry-down. The changes in the colorimetric values X, Y, Z differ depending on the halftone dot percentage (%).

In actual printing environments, it is necessary to confirm the color tones of proof sheets in view of such a dry-down phenomenon. Since it takes a long period of time for the color tones of a proof sheet to become stabilized, it has been customary for operators in the printing industry to compare a printed sample, which corresponds to a print subsequent to dry-down (hereinafter also referred to as a post-dry-down print), and a post-dry-down print, which is estimated based on experience from a print prior to dry-down (hereinafter also referred to as a pre-dry-down print). Accordingly, the adjustment of colors tends to differ depending on the experience of the operator.

According to a process of adjusting colors based on a pre-dry-down print, as disclosed in Japanese Laid-Open Patent Publication No. 2004-230793, the pre-dry-down color tones of respective colors formed on a print sheet are measured, changes caused in the post-dry-down color tones are stored in advance, and the pre-dry-down color tones are compared with pre-dry-down target values, which are represented by the sum of the changes and reference values of the post-dry-down color tones.

Japanese Laid-Open Patent Publication No. 2004-251848 discloses a color tone manager for generating a pre-dry-down profile and a post-dry-down profile, which represents a color conversion relationship from colorimetric values of a pre-dry-down color chart and colorimetric values of the post-dry-down color chart, and then simulating pre-dry-down and post-dry-down color tones using the generated profiles.

According to the above schemes of the related art, it is necessary to print a color chart of many patches in order to obtain changes in the pre-dry-down and post-dry-down color tones, or to obtain pre-dry-down calorimetric values. A color chart made up of combinations of four colors C, M, Y, K, for example, needs to have about one thousand patches in order to produce highly accurate color adjustments. Since a considerable period of time is required to calorimetrically measure so many patches, the colors of the patches tend to vary during measurement, as shown in FIG. 8. As a result, the obtained colorimetric values are of low reliability.

SUMMARY OF THE INVENTION

It is a general object of the present invention to provide a method and system for predicting print colors of a print easily and highly accurately prior to dry-down.

A major object of the present invention is to provide a method and system for predicting the print colors of a print easily and highly accurately prior to dry-down, without the need for calorimetrically measuring a large number of color charts.

Another object of the present invention is to provide a method and system for predicting the print colors of a print by generating a pre-dry-down proof sheet for the print with high accuracy.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 14 is a diagram illustrative of dry-down effective on calorimetric values Z.

DESCRIPTION OF THE PREFERRED EMBODIMENT

Figure 1:
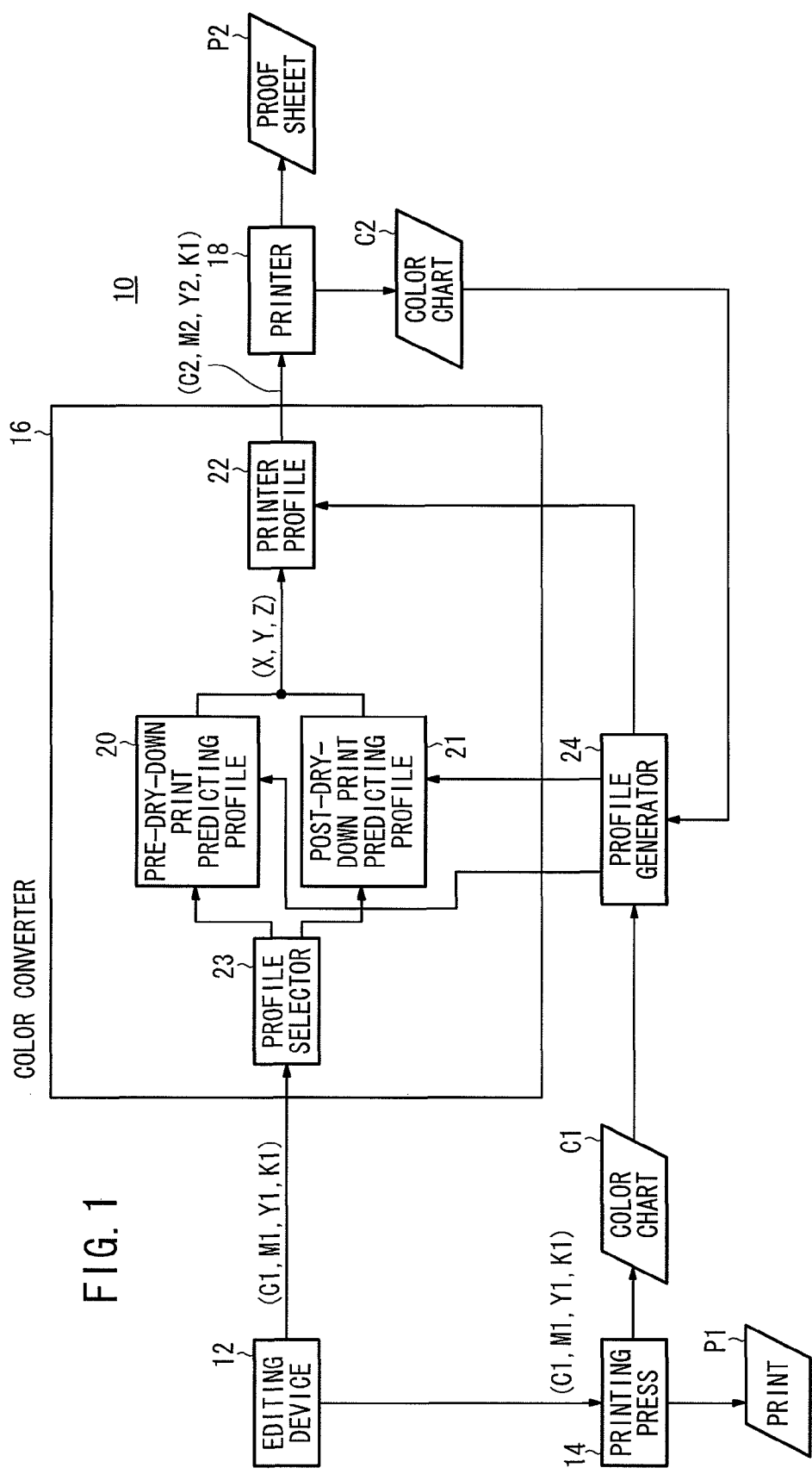
FIG. 1 is a block diagram of an overall arrangement of a print color predicting system according to an embodiment of the present invention.

FIG. 1 shows in block form a print color predicting system 10 according to an embodiment of the present invention. As shown in FIG. 1, the print color predicting system 10 comprises an editing device 12 for editing CMYK image data C1, M1, Y1, K1 for controlling colors C, M, Y, K, a printing press 14 for producing a print P1 based on the edited CMYK image data C1, M1, Y1, K1, a color converter 16 for converting the CMKY image data C1, M1, Y1, K1 into CMYK image data C2, M2, Y2, K2 for predicting colors, a printer (proof output means) 18 for generating a proof sheet P2 for the print P1 based on the CMYK image data C2, M2, Y2, K2, and a profile generator 24 for generating a pre-dry-down print predicting profile 20, a post-dry-down print predicting profile 21, and a printer profile (output profile) 22, which are incorporated in the color converter 16. The color converter 16 includes a profile selector 23 for selecting the pre-dry-down print predicting profile 20 or the post-dry-down print predicting profile 21.

The pre-dry-down print predicting profile 20 is a profile for predicting device-independent colorimetric values (predictive colorimetric values), e.g., tristimulus values X, Y, Z, of a pre-dry-down print P1 generated by the printing press 14. The pre-dry-down print predicting profile 20 is generated by the profile generator 24 based on known CMYK image data (device-dependent data), the differences between the calorimetric values of pre-dry-down and post-dry-down color charts C1 (pre-dry-down and post-dry-down colorimetric values) generated from the CMYK image data by the printing press 14, and the colorimetric values of the post-dry-down color chart C1.

The post-dry-down print predicting profile 21 is a profile for predicting device-independent calorimetric values (predictive colorimetric values) of a post-dry-down print P1 generated by the printing press 14. The post-dry-down print predicting profile 21 is generated by the profile generator 24 based on the known CMYK image data, and the colorimetric values of the post-dry-down color chart C1 generated from the CMYK image data by the printing press 14.

The printer profile 22 is a profile for converting device-independent colorimetric values of a print P1 predicted by the pre-dry-down print predicting profile 20 or the post-dry-down print predicting profile 21, e.g., colorimetric values X, Y, Z, into CMYK image data depending on output characteristics of the printer 18. The printer profile 22 is generated by the profile generator 24 based on known CMYK image data, and calorimetric values of a color chart C2 that is produced from the CMYK image data by the printer 18.

Figure 2:
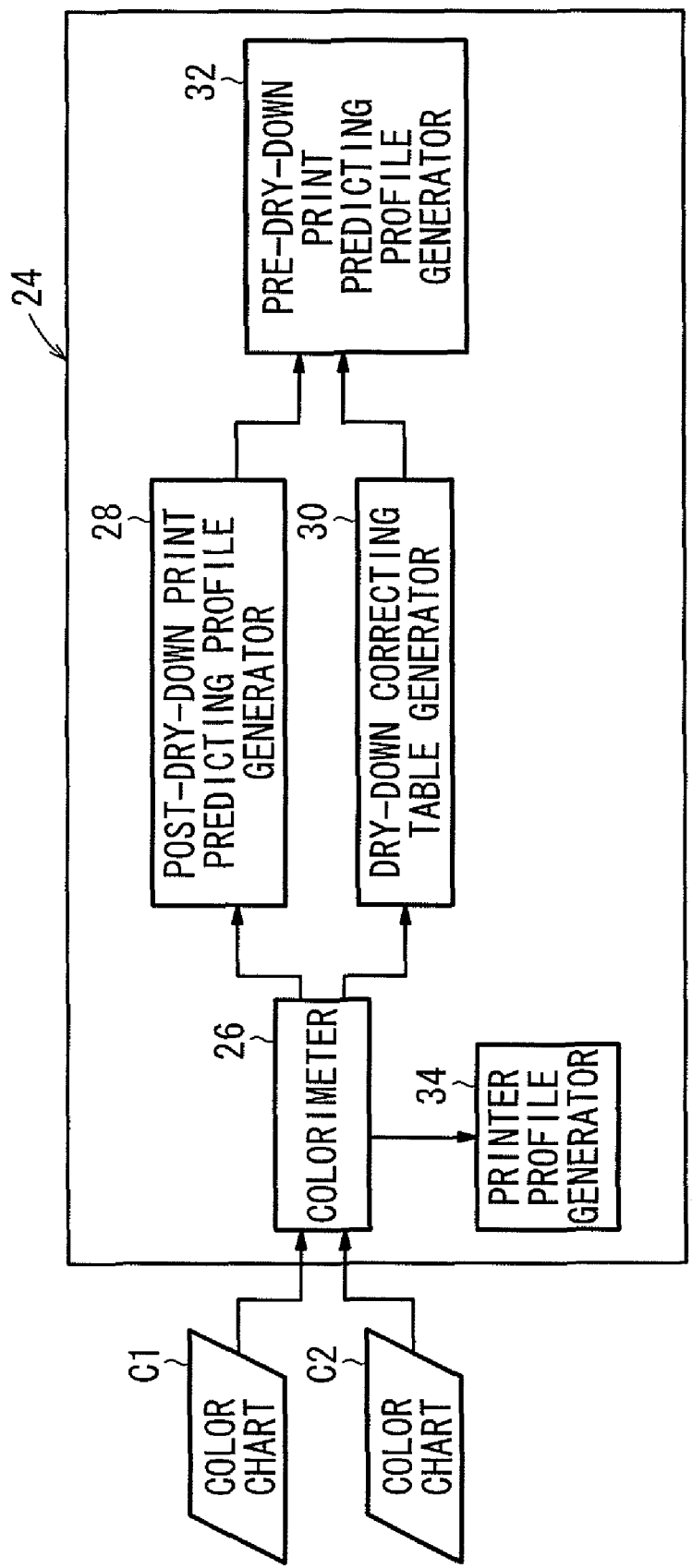
FIG. 2 is a block diagram of a profile generator of the print color predicting system shown in FIG. 1.

FIG. 2 shows an arrangement of the profile generator 24 in block form. As shown in FIG. 2, the profile generator 24 includes a colorimeter 26 for measuring colorimetric values of color charts C1, C2, a post-dry-down print predicting profile generator 28 for generating a post-dry-down print predicting profile 21 by calorimetrically measuring a post-dry-down color chart C1, a dry-down correcting table generator (difference conversion table generator) 30 for generating a dry-down correcting table (difference conversion table) using the colorimetric values obtained by calorimetrically measuring a pre-dry-down color chart C1 and the calorimetric values obtained by calorimetrically measuring a post-dry-down color chart C1, a pre-dry-down print predicting profile generator 32 for generating a pre-dry-down print predicting profile 20 using the post-dry-down print predicting profile 21 and the dry-down correcting table, and a printer profile generator (output profile generator) 34 for generating a printer profile 22 by measuring the colorimetric values of a color chart C2 produced by the printer 18.

The print color predicting system 10 according to the present embodiment is basically constructed as described above. Next, a print color predicting method carried out by the print color predicting system 10 shall be described below.

Figure 3:
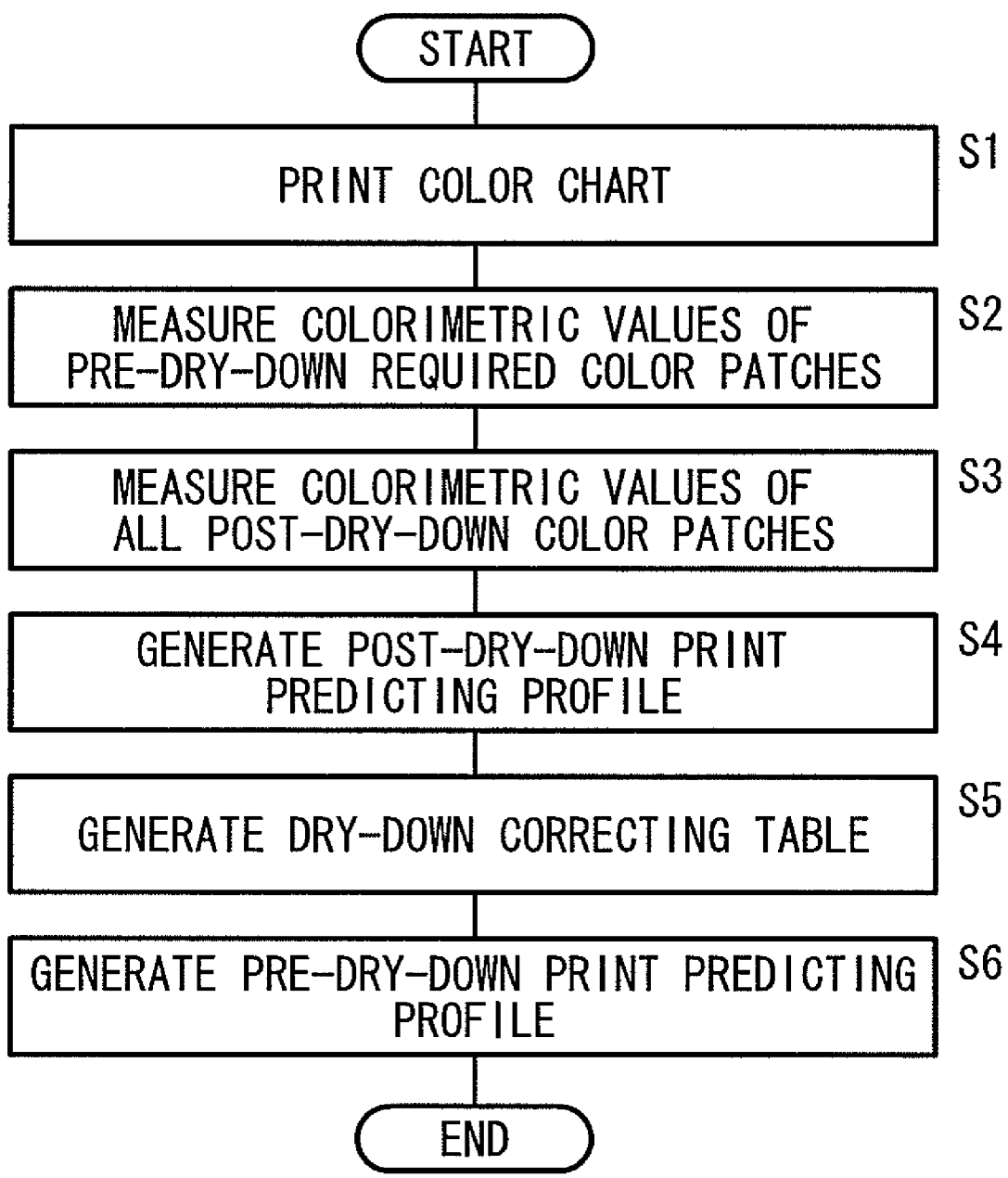
FIG. 3 is a flowchart of a sequence for generating a pre-dry-down print predicting profile.

First, a sequence for generating the pre-dry-down print predicting profile 20 and the post-dry-down print predicting profile 21 with the profile generator 24 will be described below with reference to the flowchart shown in FIG. 3.

The editing device 12 supplies known CMYK image data to the printing press 14, which prints a color chart C1 (step S1). The color chart C1 comprises a plurality of color patches 36, e.g., about one thousand color patches 36, printed in respective halftone dot percentages (%) of the CMYK image data, at predetermined intervals in a range from 0% to 100% (see FIG. 4).

Figure 4:
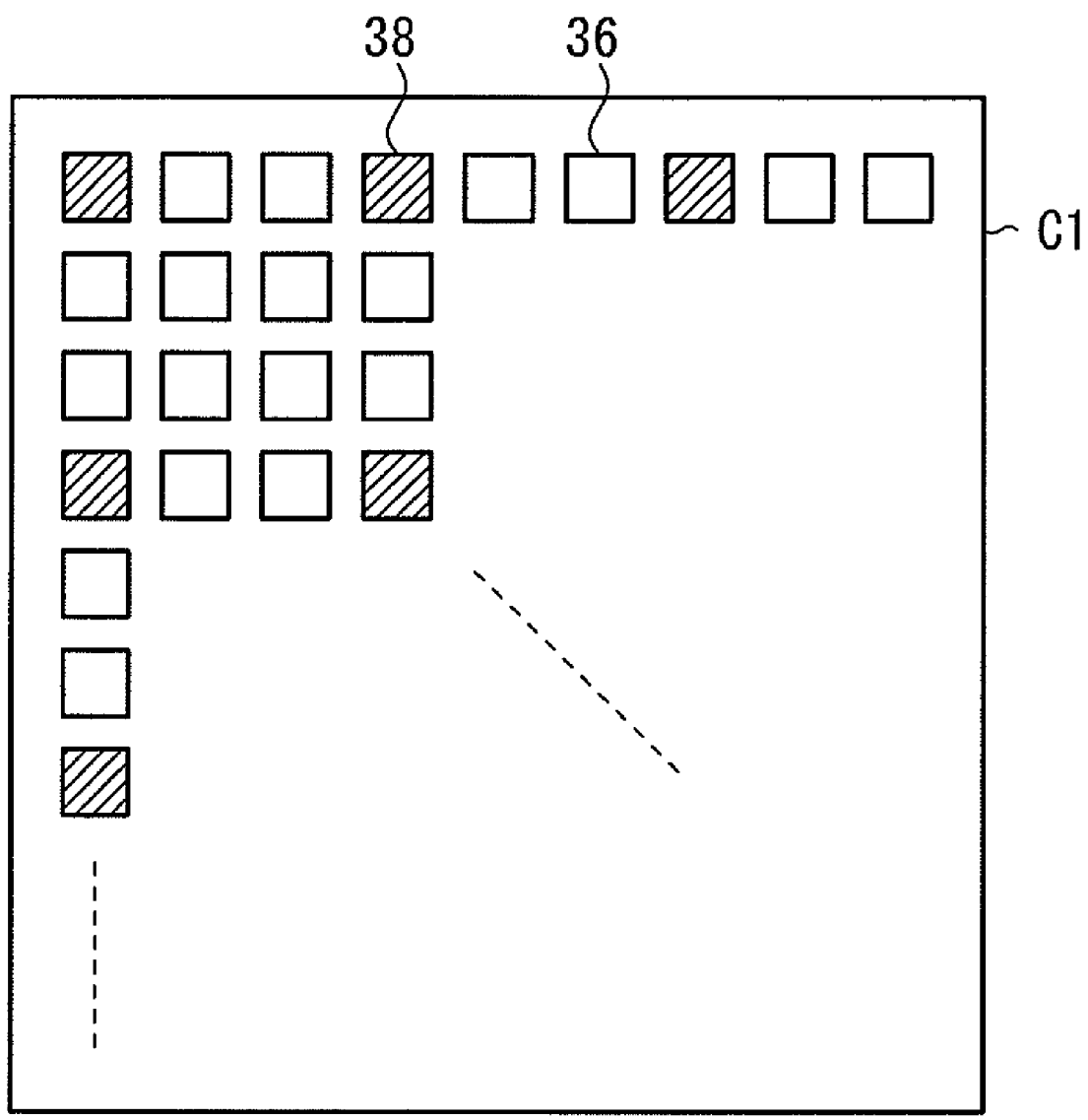
FIG. 4 is a view of a color chart for generating a pre-dry-down print predicting profile and a post-dry-down print predicting profile.

Then, immediately after the color chart C1 has been printed in step S1, certain color patches (pre-dry-down required color patches) 38 are selected from among the color patches 36 of the color chart C1, as shown in FIG. 4. The selected color patches 38 are calorimetrically measured by the colorimeter 26 (step S2).

The selected color patches 38 have halftone dot percentages (%) thereof set to 20%, 40%, 60%, 80%, and 100%, for example, and include twenty patches formed of single-color inks C, M, Y, K, fifteen patches formed of two-color inks CM, MY, CY, five patches formed of a three-color ink CMY, five patches formed of a four-color ink CMYK, and six patches formed of an ink CMY and having their halftone dot percentages (%) set to 0% or 100% and formed of an ink K and having their halftone dot percentages (%) set to 100%, wherein the six patches do not overlap with the other patches described above. These fifty-one color patches 38, because there are relatively few in number, can be measured calorimetrically by the colorimeter 26 within a very short period of time. Accordingly, a dry-down effect that occurs during the measurement thereof can be ignored, and all of the color patches 38 can be measured calorimetrically under substantially the same conditions.

Rather than selecting the color patches 38 from the color chart C1, it is preferable to generate a color chart made up of only the pre-dry-down required color patches separately from the color chart C1, and then to measure the generated color chart colorimetrically. The reason why the separately generated color chart is preferable is that if the required color patches 38 are selected from a relatively wide color chart C1 containing many color patches 36 and then calorimetrically measured, unwanted dry-down may occur while the colorimeter 26 or the color chart C1 is being moved for performing colorimetric measurement thereof. On the other hand, the separately generated color chart, which contains only the pre-dry-down required color patches, is smaller and therefore can be measured calorimetrically within a shorter period of time for obtaining desired colorimetric values prior to dry-down.

The pre-dry-down required color patches for generating the pre-dry-down print predicting profile 20 are not limited to the certain color patches 38 selected from the color patches 36, but also may be color patches produced independently from the color patches 36.

Then, after a sufficient period of time has elapsed from printing of the color patch C1, the color chart C1 has gone through dry-down, and the color tones thereof become stabilized. All of the color patches (post-dry-down all color patches) 36, including the color patches 38, are measured calorimetrically by the colorimeter 26 (step S3).

Inasmuch as the color chart C1 contains about one thousand color patches 36 therein, it takes a considerable period of time to calorimetrically measure all of the color patches 36. However, the calorimetric values obtained from the color chart C1 are stable, because a sufficient period of time has elapsed from printing of the color patch C1.

The post-dry-down print predicting profile generator 28 generates a post-dry-down print predicting profile 21 for determining post-dry-down tristimulus values Xa, Ya, Za with respect to the CMYK image data, using the known CMYK image data used to generate the color chart C1 and the calorimetric values, e.g., tristimulus values Xa, Ya, Za, of all of the post-dry-down color patches 36 of the color chart C1, which have been colorimetrically measured in step S3 (step S4). The generated post-dry-down print predicting profile 21 is set in the color converter 16 of the print color predicting system 10.

Then, the dry-down correcting table generator 30 determines colorimetric value differences dX, dY, dZ between the colorimetric values of the pre-dry-down color patches 38 acquired in step S2, e.g., tristimulus values Xb, Yb, Zb, and the calorimetric values of the post-dry-down color patches 38 acquired in step S3, e.g., tristimulus values Xa, Ya, Za. The dry-down correcting table generator 30 generates a dry-down correcting table for converting the CMYK image data into calorimetric value differences dX, dY, dZ, using the determined calorimetric value differences dX, dY, dZ and the known CMYK image data used to generate the color chart C1 (step S5). It is assumed that dX=Xa−Xb, dY=Ya−Yb, and dZ=Za−Zb.

The few pre-dry-down color patches 38, i.e., the fifty-one pre-dry-down color patches 38, are measured colorimetrically in step S2 in order to shorten the colorimetric measuring time thereof. The calorimetric values obtained from only a small number of pre-dry-down color patches 38 provide a rough associative relationship between the CMYK image data (device-dependent data) and the colorimetric value differences dX, dY, dZ. The dry-down correcting table serves to interpolate the colorimetric value differences dX, dY, dZ and convert the CMYK image data (device-dependent data) into interpolated values of the colorimetric value differences dX, dY, dZ. Since the colorimetric value differences dX, dY, dZ represent differential values, they are considerably smaller than the colorimetric values for the pre-dry-down color patches 38, and hence errors in the interpolated values of the colorimetric value differences dX, dY, dZ are small. Therefore, the dry-down correcting table, which is generated using the interpolated values of the colorimetric value differences dX, dY, dZ, is as accurate as the post-dry-down print predicting profile 21.

Figure 5:
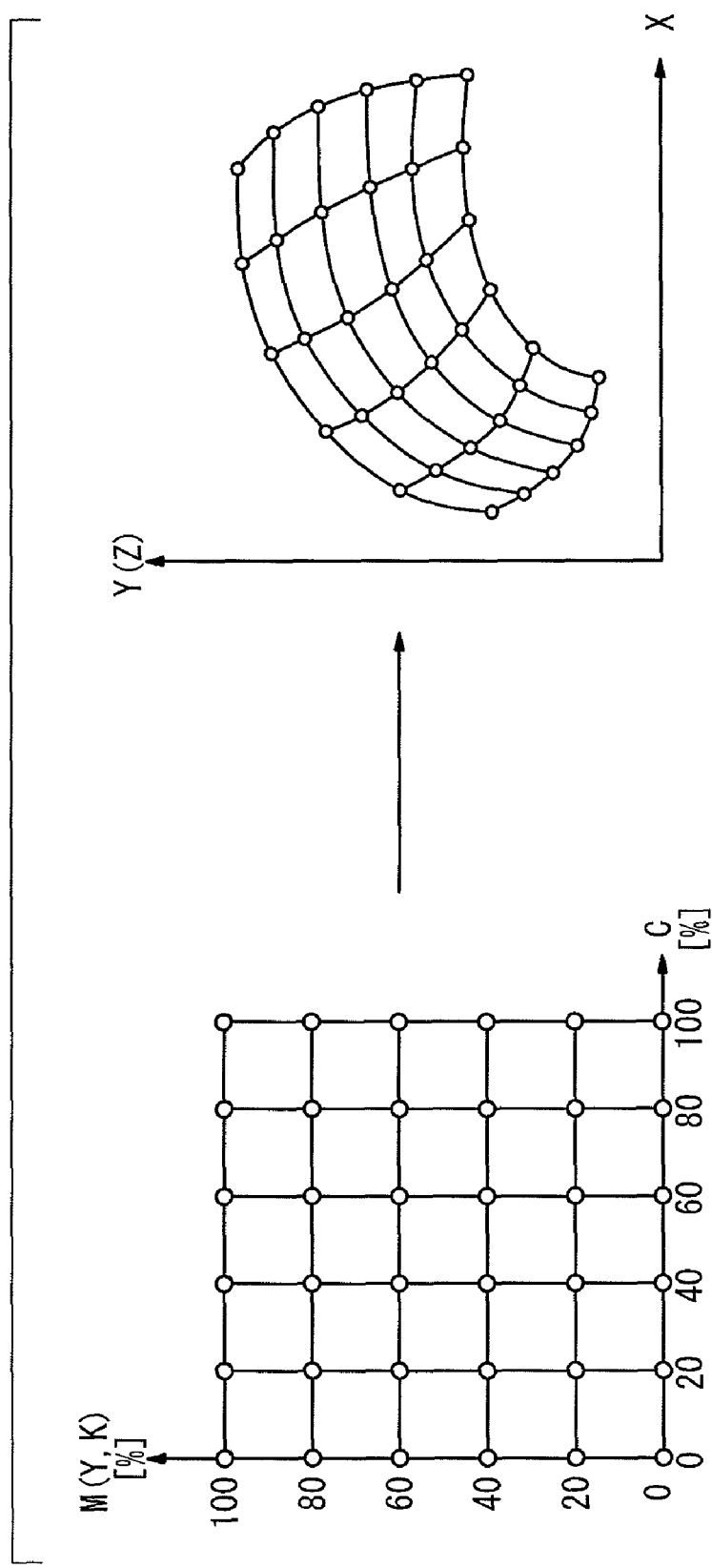
FIG. 5 is a diagram showing the relationship between CMYK image data and tristimulus values (X, Y, Z)

As shown in FIG. 5, the relationship between the CMYK image data and the tristimulus values X, Y, Z is nonlinear. The colorimetric value differences dX, dY, dZ are estimated in view of such a nonlinear relationship, as shown in FIG. 5. The colorimetric value differences dX, dY, dZ may be estimated according to the method disclosed in Japanese Laid-Open Patent Publication No. 2006-024971, for example.

The pre-dry-down print predicting profile generator 32 generates a pre-dry-down print predicting profile 20, which represents the relationship between the CMYK image data and the pre-dry-down tristimulus values Xb, Yb, Zb, by subtracting the interpolated values of the colorimetric value differences dX, dY, dZ of the dry-down correcting table generated in step S5 from the tristimulus values Xa, Ya, Za of the post-dry-down print predicting profile 21 generated in step S4 (step S6). The generated pre-dry-down print predicting profile 20 is set in the color converter 16 of the print color predicting system 10.

If the colorimetric value differences dX, dY, dZ are determined as dX=Xb−Xa, dY=Yb−Ya, and dZ=Zb−Za in step S5, then the pre-dry-down print predicting profile generator 32 generates a pre-dry-down print predicting profile 20 by adding the interpolated values of the colorimetric value differences dX, dY, dZ of the dry-down correcting table, as generated in step S5, to the tristimulus values Xa, Ya, Za of the post-dry-down print predicting profile 21, as generated in step S4.

In the above description, the pre-dry-down print predicting profile 20 immediately after the color chart C1 has been printed is generated by colorimetrically measuring the color patches 36 of the color chart C1, immediately after printing of the color chart C1. However, the color patches 36 of the color chart C1 can be measured colorimetrically at different times, e.g., 5 minutes, 10 minutes, 20 minutes, and 30 minutes, after printing of the color chart C1, whereupon a plurality of pre-dry-down print predicting profiles 20 may be generated at different times respectively.

If such plural pre-dry-down print predicting profiles 20 are generated at respective different times, a pre-dry-down print predicting profile 20 upon elapse of a desired period of time can be calculated by any of linear interpolation, spline interpolation, polynomial approximation, or the like.

Figure 6:
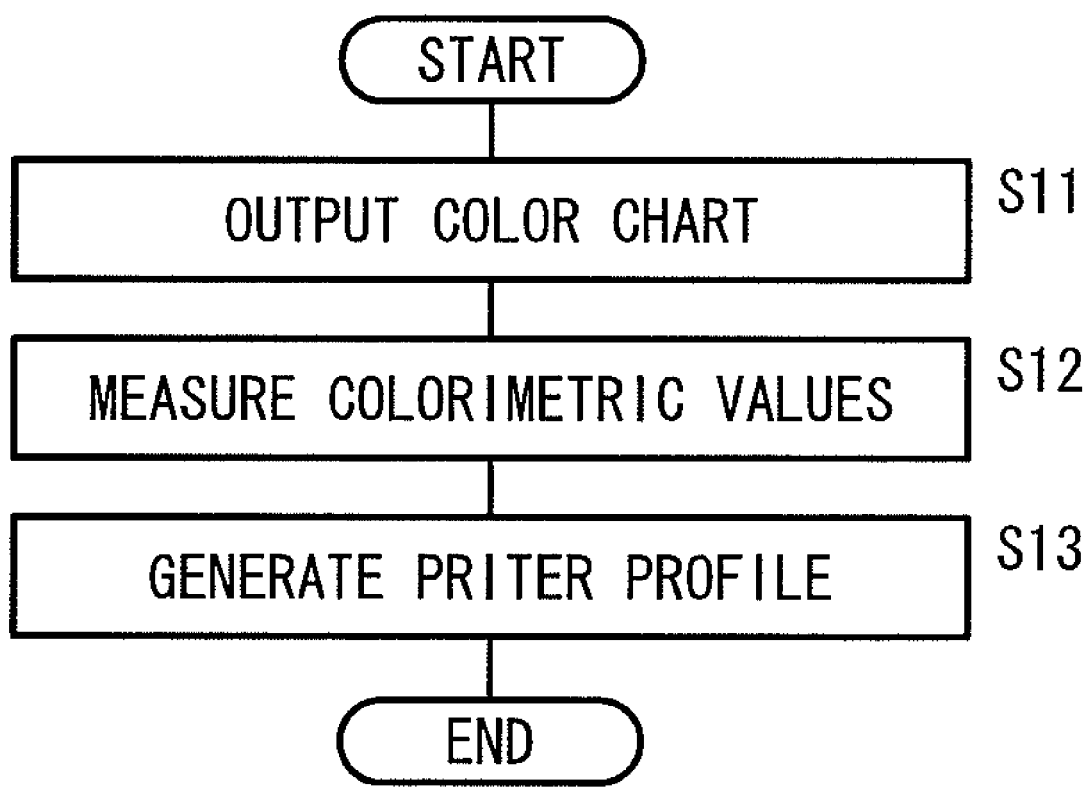
FIG. 6 is a flowchart of a sequence for generating a printer profile.

A sequence for generating a printer profile 22 with the profile generator 24 will be described below with reference to FIG. 6.

The color converter 16 supplies known CMYK image data to the printer 18, which outputs a color chart C2 made up of a plurality of color patches on a recording medium (step S11), in the same manner as printing for the color chart C1 (in step S1).

After the color tones of the color chart C2 have become stabilized, upon elapse of a sufficient period of time after printing of the color chart C2, the colorimeter 26 calorimetrically measures the color patches of the color chart C2 to determine tristimulus values X, Y, Z (step S12). The printer profile generator 34 generates a printer profile 22, which represents the relationship between the tristimulus values X, Y, Z and the CMYK image data used to generate the color chart C2 (step S13). The generated printer profile 22 then is set in the color converter 16.

After the pre-dry-down print predicting profile 20, the post-dry-down print predicting profile 21, and the printer profile 22 have been generated, the print color predicting system 10 generates a proof sheet P2, and adjusts printing conditions, etc., based on the generated proof sheet P2.

Figure 7:
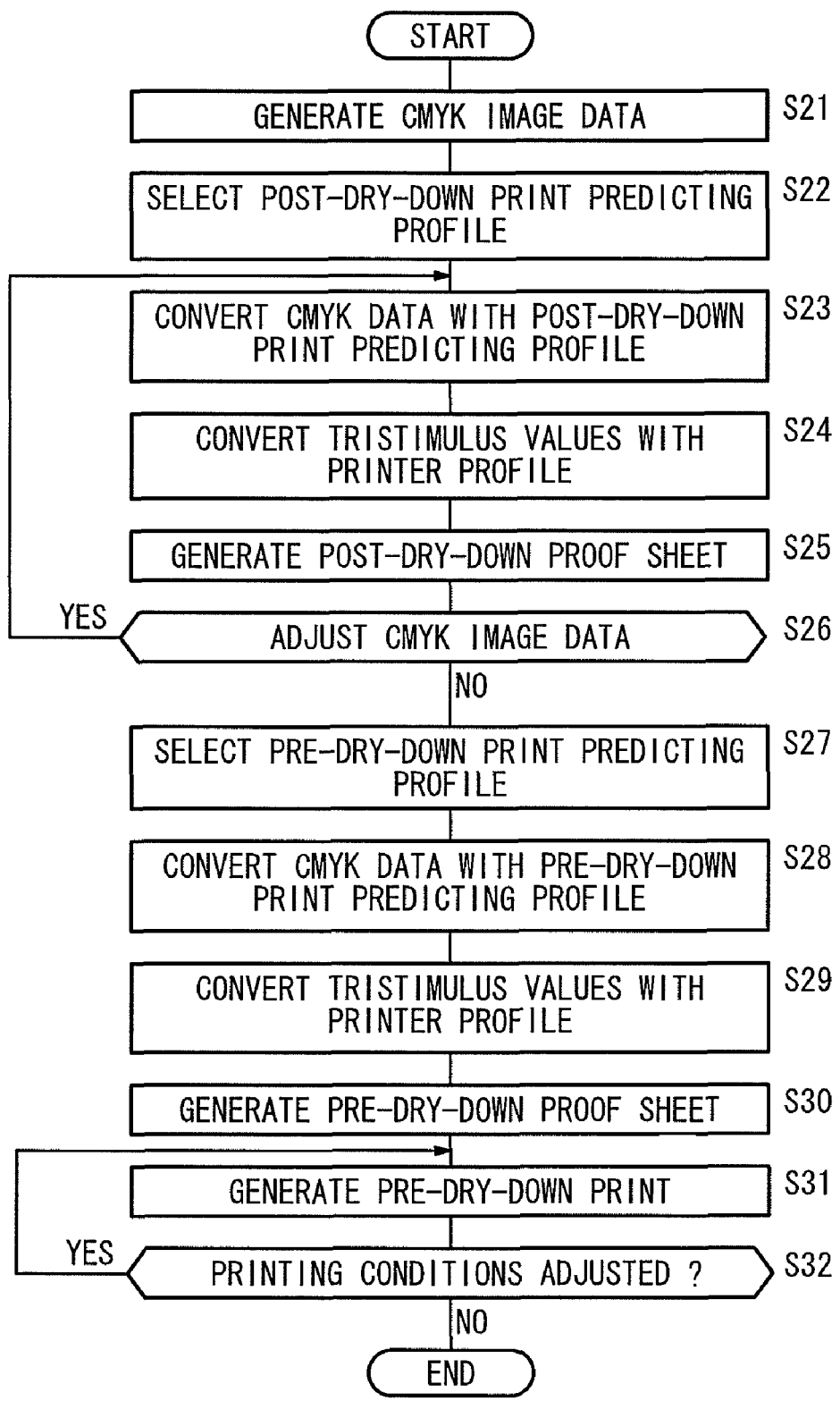
FIG. 7 is a flowchart of a sequence for adjusting printing conditions.
Figure 8:
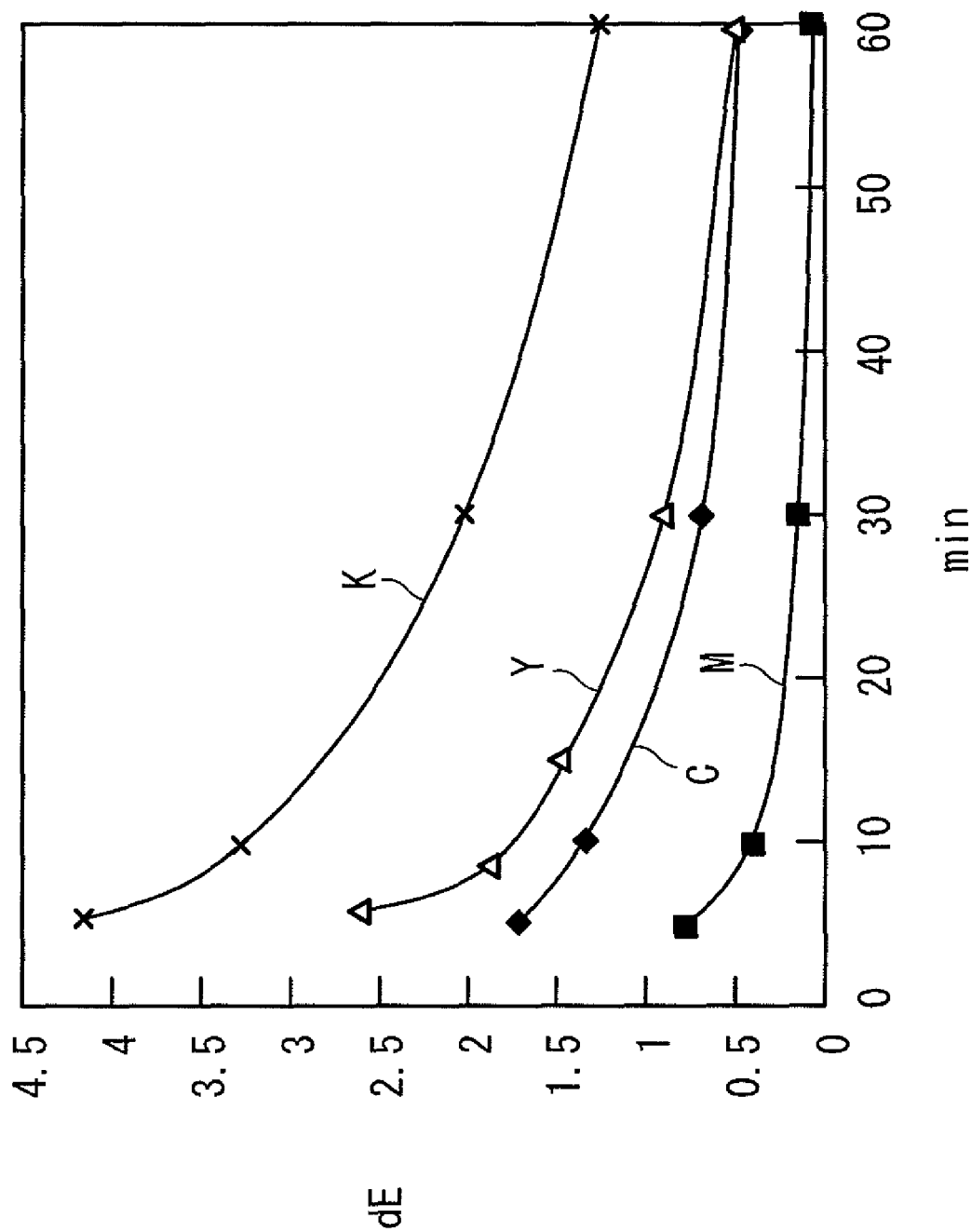
FIG. 8 is a diagram illustrative of color differences caused by dry-down.
Figure 9:
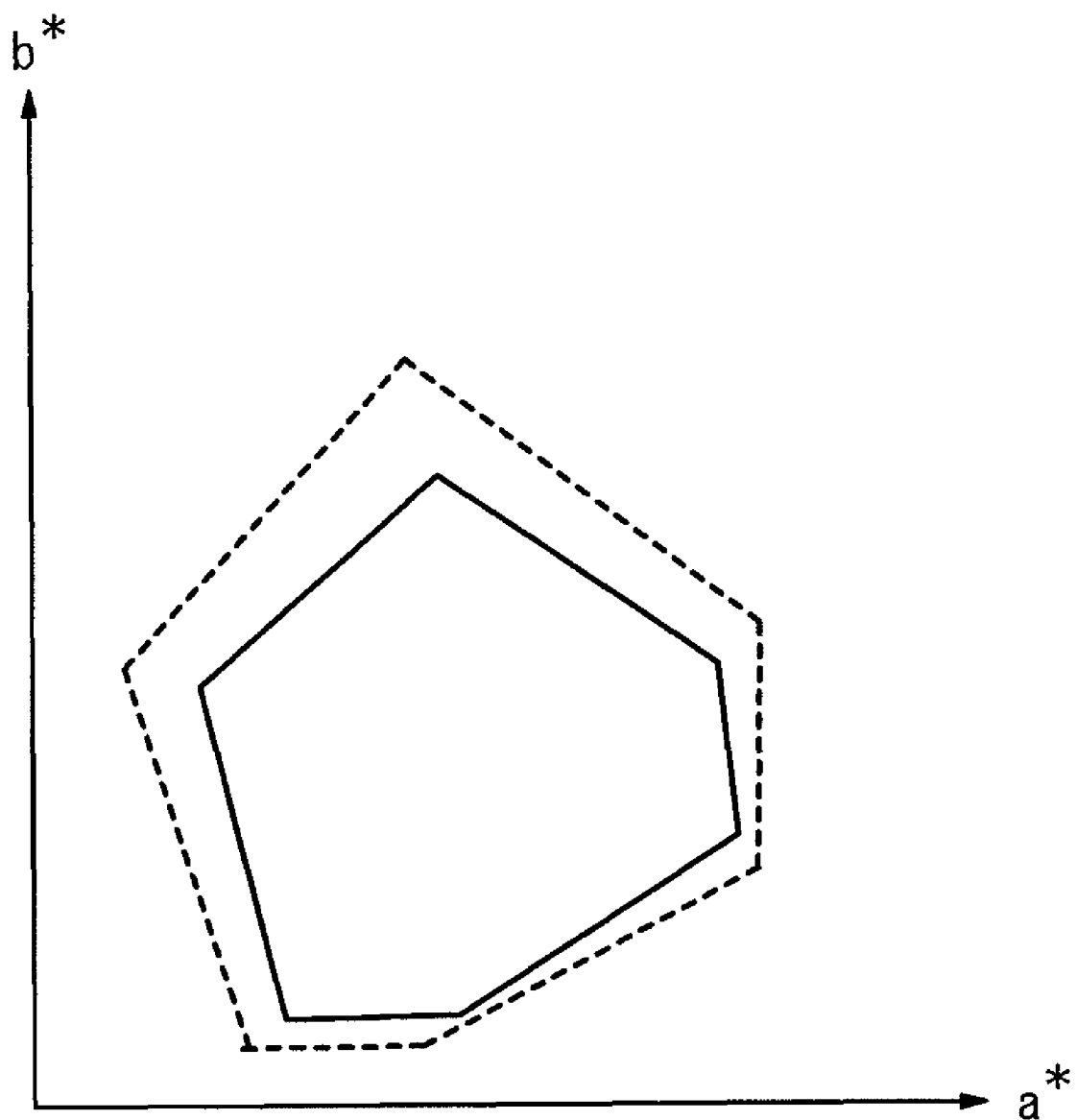
FIG. 9 is a diagram illustrative of dry-down occurring in an a*b* plane.
Figure 10:
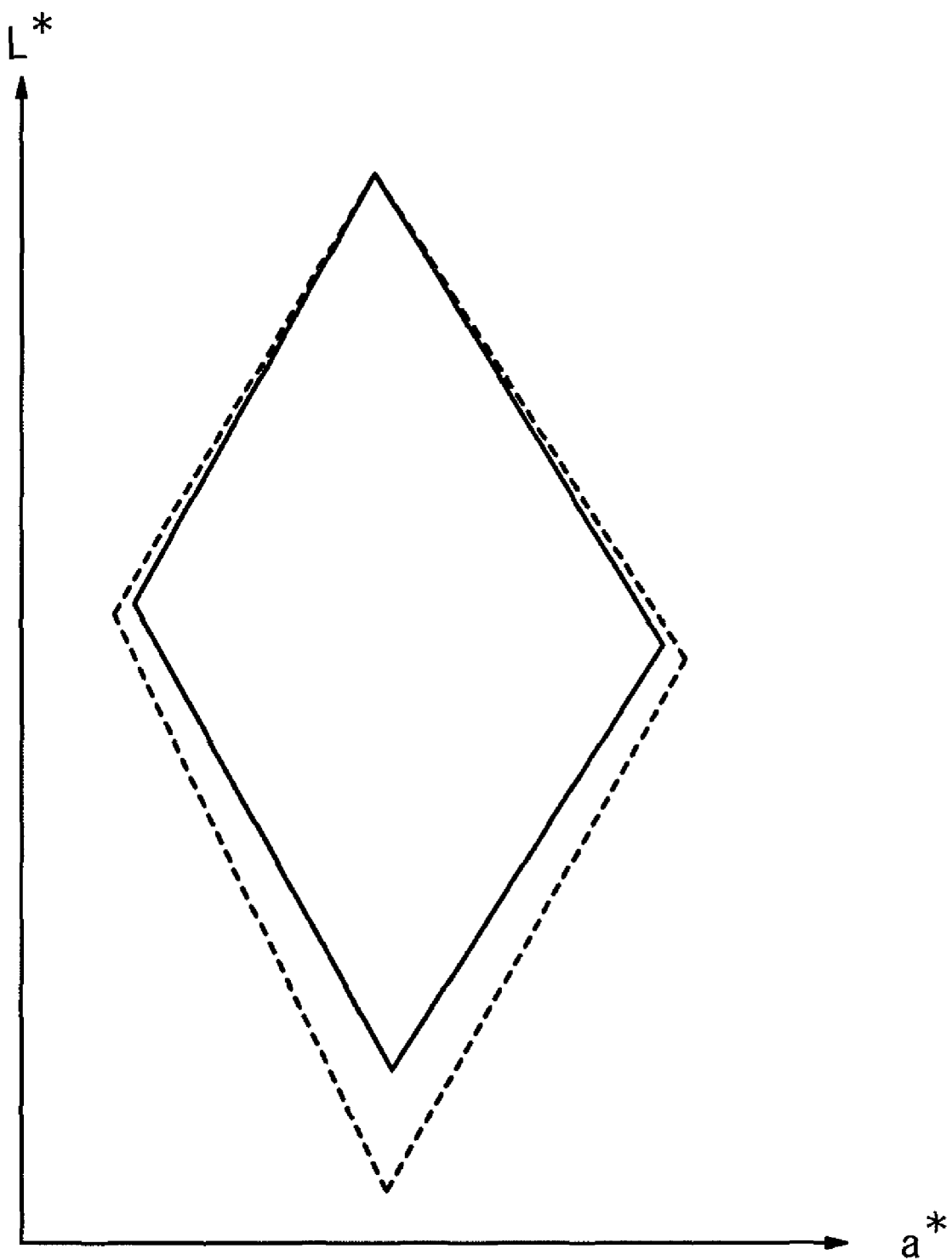
FIG. 10 is a diagram illustrative of dry-down occurring in an L*a* plane.
Figure 11:
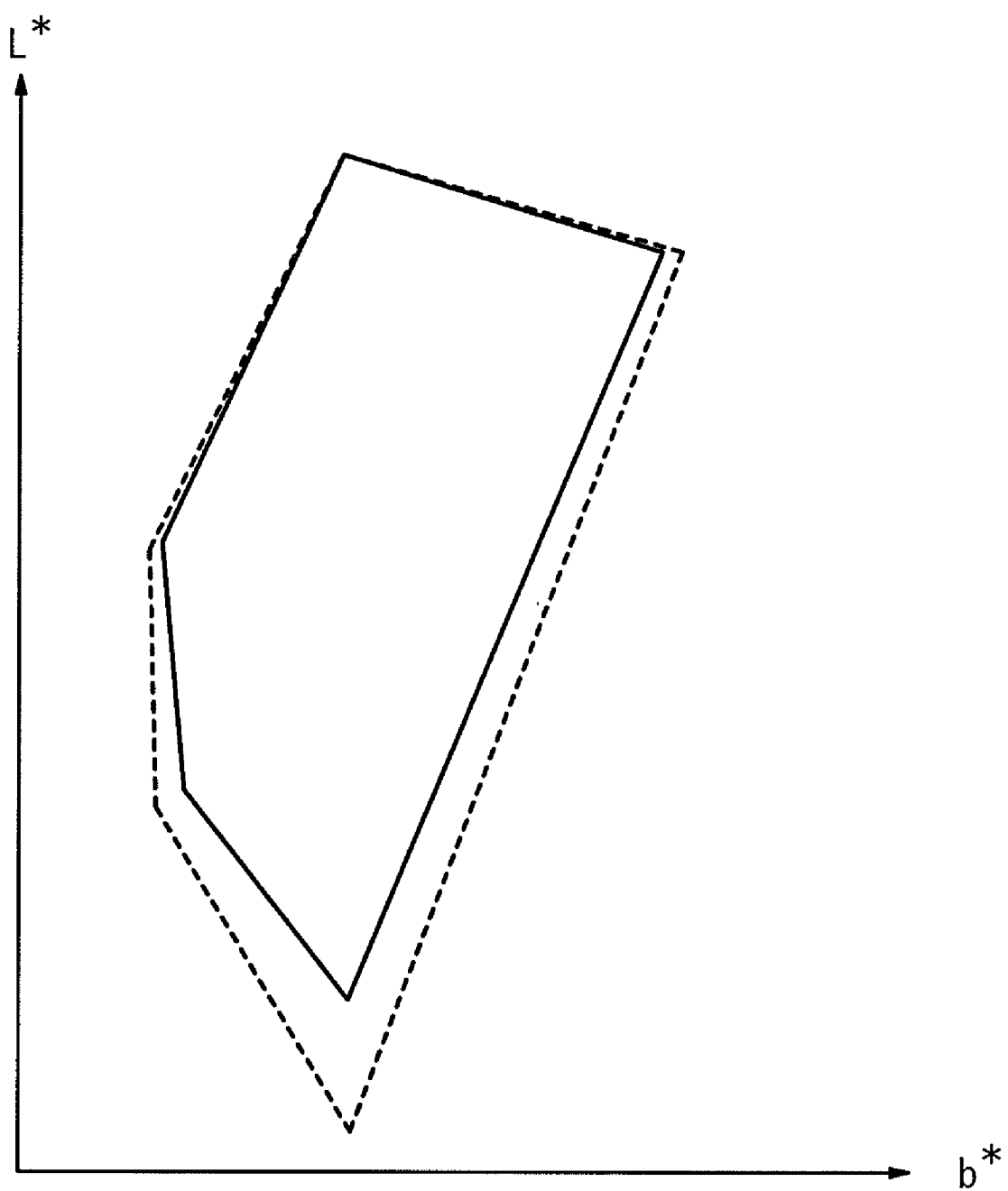
FIG. 11 is a diagram illustrative of dry-down occurring in an L*b* plane.
Figure 12:
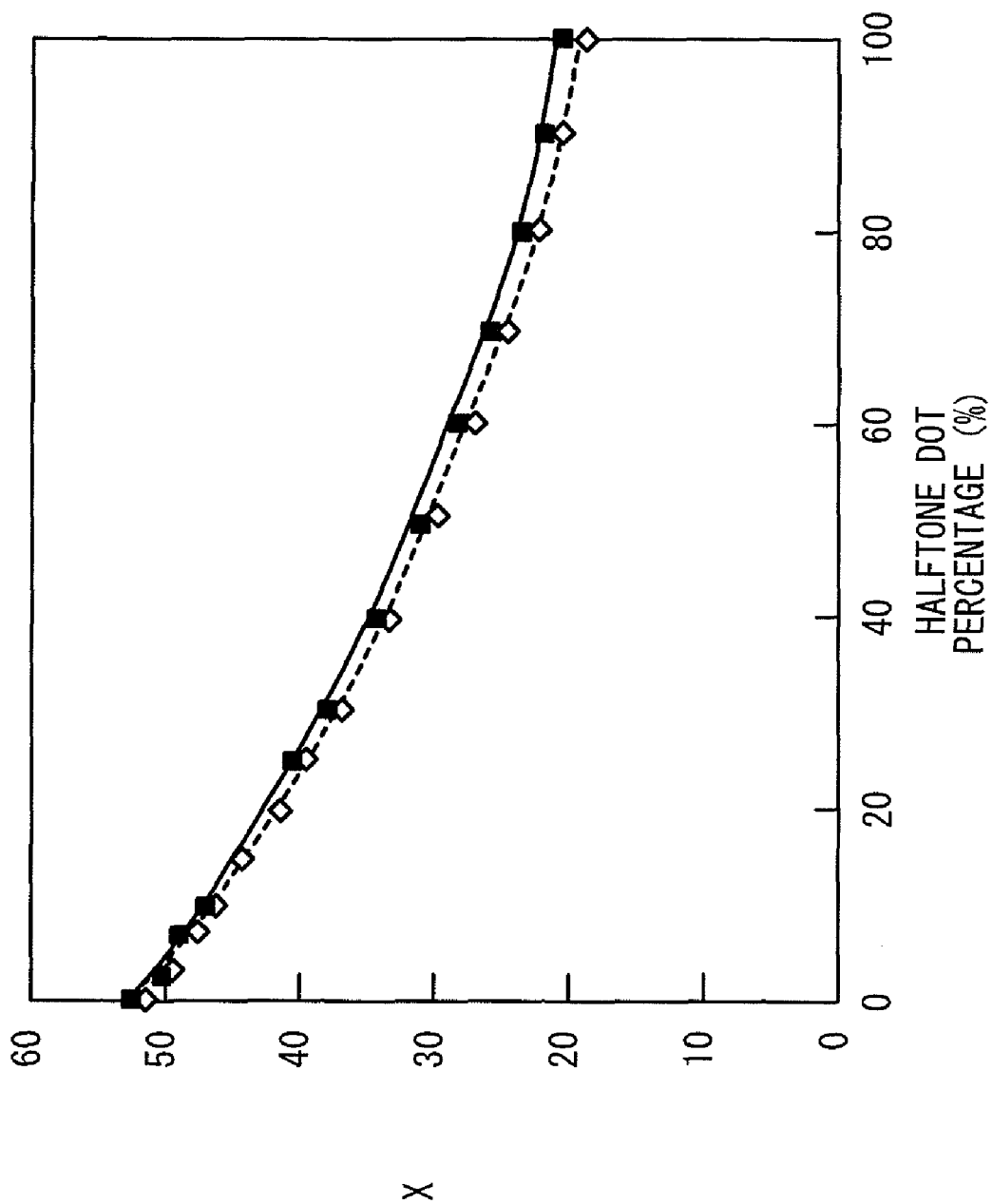
FIG. 12 is a diagram illustrative of dry-down effective on calorimetric values X.
Figure 13:
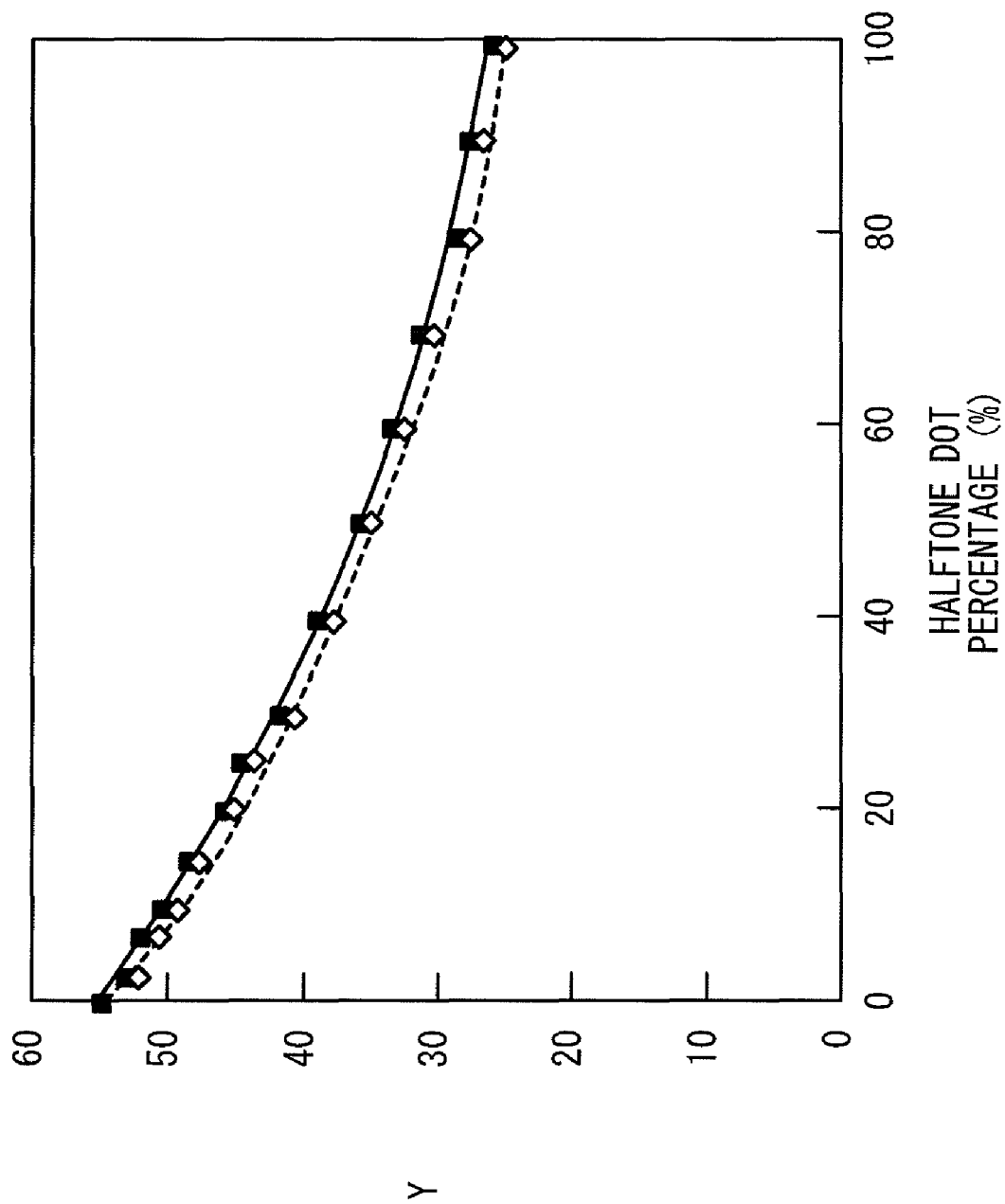
FIG. 13 is a diagram illustrative of dry-down effective on calorimetric values Y.

A sequence for generating a proof sheet P2 and adjusting printing conditions, etc., will be described below with reference to FIG. 7.

The editing device 12 generates desired CMYK image data C1, M1, Y1, K1 (step S21) and supplies the generated CMYK image data C1, M1, Y1, K1 to the color converter 16. In the color converter 16, the profile selector 23 selects the post-dry-down print predicting profile 21 (step S22). The post-dry-down print predicting profile 21 converts the CMYK image data C1, M1, Y1, K1, which are device-dependent data, into tristimulus values X, Y, Z, which are device-independent data (step S23).

The printer profile 22 converts the tristimulus values X, Y, Z into CMYK image data C2, M2, Y2, K2, which are dependent on the output characteristics of the printer 18 (step S24). The printer 18 then generates a proof sheet P2 for a post-dry-down print P1 using the CMYK image data C2, M2, Y2, K2 (step S25).

The operator confirms the proof sheet P2. If necessary, the operator adjusts the CMYK image data C1, M1, Y1, K1 (step S26) and repeats the processing of steps S23 through S26 until a desired post-dry-down proof sheet P2 is obtained.

After the desired post-dry-down proof sheet P2 has been obtained, the profile selector 23 selects the pre-dry-down print predicting profile 20 (step S27). It is assumed that a profile corresponding to the post-printing elapsed time for confirming a print P1 is selected as the pre-dry-down print predicting profile 20.

Using the selected pre-dry-down print predicting profile 20, the CMYK image data C1, M1, Y1, K1 adjusted in step S26 are converted into tristimulus values X, Y, Z (step S28). Then, the tristimulus values X, Y, Z are converted by the printer profile 22 into CMYK image data C2, M2, Y2, K2, which are dependent on the output characteristics of the printer 18 (step S29). Using the CMYK image data C2, M2, Y2, K2, the printer 18 generates a proof sheet P2 for a pre-dry-down print P1 upon elapse of a desired time (step S30).

The printer 14 generates a print P based on the CMYK image data C1, M1, Y1, K1 adjusted in step S26 (step S31). The operator compares the pre-dry-down print P1 and the pre-dry-down proof sheet P2. If the colors of the pre-dry-down print P1 and the pre-dry-down proof sheet P2 do not agree with each other, then the operator makes fine adjustments to the printing conditions, such as solid densities, etc., of the printing press 14 (step S32). The processing of steps S31 and S32 is repeated until the colors of the pre-dry-down print P1 and the pre-dry-down proof sheet P2 agree with each other. As a consequence, the printing conditions can easily and appropriately be adjusted using the pre-dry-down print P1, without relying excessively on the experience of the operator.

In the above embodiment, the pre-dry-down print predicting profile 20 is generated, and the proof sheet P2 for the pre-dry-down print P1 is generated using the pre-dry-down print predicting profile 20. However, the proof sheet P2 for the pre-dry-down print P1 may also be generated by producing an arbitrary print P1, measuring colorimetric values of the arbitrary print P1 subsequent to dry-down, and then correcting the colorimetric values of the arbitrary print P1 using the dry-down correcting table generated by the dry-down correcting table generator 30.

In the above embodiment, the color converter 16 determines tristimulus values X, Y, Z from the CMYK image data C1, M1, Y1, K1 using the pre-dry-down print predicting profile 20 or the post-dry-down print predicting profile 21, and thereafter, the color converter 16 determines the CMYK image data C2, M2, Y2, K2 from the tristimulus values X, Y, Z using the printer profile 22. However, the color converter 16 also may determine the CMYK image data C2, M2, Y2, K2 from the CMYK image data C1, M1, Y1, K1, via colorimetric values L*, a*, b*, rather than by the tristimulus values X, Y, Z.

The pre-dry-down print predicting profile 20, or the post-dry-down print predicting profile 21 and the printer profile 22, may be combined into a single profile, and the color converter 16 may determine the CMYK image data C2, M2, Y2, K2 directly from the CMYK image data C1, M1, Y1, K1, using the single profile.

In the print color predicting system 10, the printer 18 generates the proof sheet P2. However, the proof sheet P2 may be displayed on a color monitor (proof output means), rather than being generated by the printer 18. If the proof sheet P2 is displayed on a color monitor, then the profile generator 24 generates a monitor profile (output profile) by calorimetrically measuring the color chart C2 displayed on the color monitor, and then sets the monitor profile in the color converter 16.

The print color predicting system 10 is not limited to generating a profile for device-dependent data in four colors C, M, Y, K, but is also applicable to generating a pre-dry-down print predicting profile 20 for device-dependent data in any number of colors, e.g., two or more colors.

Although a certain preferred embodiment of the present invention has been shown and described in detail, it should be understood that various changes and modifications may be made to the disclosed embodiment without departing from the scope of the invention as set forth in the appended claims.

What is claimed is:

1. A method of predicting colors of a print produced by a printing press, comprising the steps of:

using at least one colorimeter to perform:
colorimetrically measuring a color chart prior to dry-down, which is generated based on device-dependent data by the printing press, thereby obtaining pre-dry-down colorimetric values; and
colorimetrically measuring the color chart subsequent to dry-down, thereby obtaining post-dry-down colorimetric values; and using at least one processor to perform:
calculating colorimetric value differences with respect to said device-dependent data between said pre-dry-down colorimetric values and said post-dry-down colorimetric values; and
calculating colorimetric value differences with respect to arbitrary device-dependent data by interpolating the first-mentioned colorimetric value differences, and calculating pre-dry-down colorimetric values with respect to said arbitrary device-dependent data, using the calculated second-mentioned colorimetric value differences and post-dry-down colorimetric values with respect to said arbitrary device-dependent data; and
predicting the colors of said print prior to pre-dry-down based on the calculated pre-dry-down colorimetric values with respect to the arbitrary device-dependent data.

2. A method according to claim 1, further comprising the steps of:

generating a difference conversion table for converting the device-dependent data into colorimetric value differences between said pre-dry-down colorimetric values and said post-dry-down colorimetric values, using said device-dependent data used to generate said color chart and the colorimetric value differences with respect to the device-dependent data between said pre-dry-down colorimetric values and said post-dry-down colorimetric values; and calculating the colorimetric value differences with respect to said arbitrary device-dependent data by interpolating said difference conversion table.

3. A method according to claim 2, further comprising the steps of:
generating a post-dry-down print predicting profile for determining post-dry-down colorimetric values with respect to the device-dependent data, using the device-dependent data and the post-dry-down colorimetric values of the color chart generated by said printing press based on said device-dependent data;
generating a pre-dry-down print predicting profile for determining pre-dry-down colorimetric values with respect to the device-dependent data, using said post-dry-down print predicting profile and the interpolated difference conversion table; and
calculating the pre-dry-down colorimetric values with respect to said arbitrary device-dependent data, using said pre-dry-down print predicting profile.

4. A method according to claim 1, further comprising the steps of:
measuring a plurality of sets of the pre-dry-down colorimetric values at different elapsed times from generation of said color chart; and
calculating pre-dry-down colorimetric values at an arbitrary elapsed time from generation of said color chart by interpolating the pre-dry-down colorimetric values at the respective elapsed times.

5. A system for predicting colors of a print produced by a printing press, comprising:
a colorimeter for colorimetrically measuring a color chart, which is generated based on device-dependent data by the printing press, thereby obtaining colorimetric values;
a difference conversion table generator for generating a difference conversion table for converting the device-dependent data into colorimetric value differences between pre-dry-down colorimetric values and post-dry-down colorimetric values, using colorimetric value differences between pre-dry-down colorimetric values obtained by measuring said color chart prior to dry-down and post-dry-down colorimetric values obtained by measuring said color chart subsequent to dry-down;
a post-dry-down print predicting profile generator for generating a post-dry-down print predicting profile for determining post-dry-down colorimetric values with respect to the device-dependent data; and
a pre-dry-down print predicting profile generator for generating a pre-dry-down print predicting profile for determining pre-dry-down colorimetric values with respect to the device-dependent data, using the difference conversion table and said post-dry-down print predicting profile,
wherein the colors of said print are predicted by calculating pre-dry-down colorimetric values with respect to arbitrary device-dependent data using said pre-dry-down print predicting profile.

6. A system according to claim 5, further comprising: proof output means for outputting a proof sheet for the print; and
an output profile generator for generating an output profile for determining device-dependent data with respect to colorimetric values, using colorimetric values of a color chart generated by said proof output means based on the device-dependent data, and said device-dependent data;
wherein device-dependent data with respect to said pre-dry-down colorimetric values are determined using said output profile, and said proof output means outputs the proof sheet using said device-dependent data.

7. A system for predicting colors of a print produced by a printing press, comprising:
proof output means for outputting a proof sheet for the print;
a pre-dry-down print predicting profile for determining predicted colorimetric values of the print prior to dry down, which is generated by said printing press, from device-dependent data;
a post-dry-down print predicting profile for determining predicted colorimetric values of the print subsequent to dry-down, which is generated by said printing press, from device-dependent data;
a profile selector for selecting said pre-dry-down print predicting profile or said post-dry-down print predicting profile; and
an output profile for determining device-dependent data of said proof output means from said predicted colorimetric values,
wherein predicted colorimetric values of the print are determined from arbitrary device-dependent data, using said pre-dry-down print predicting profile or said post-dry-down print predicting profile, which is selected by said profile selector, device-dependent data are determined from said predicted colorimetric values of the print prior to dry down or said predicted colorimetric values of the print subsequent to dry down using the output profile, and said proof output means outputs the proof sheet using said device-dependent data;
the colors of the print is predicted using the proof sheet.

* * * * *